United States Patent [19]
Chernoff et al.

[11] Patent Number: 5,304,219
[45] Date of Patent: Apr. 19, 1994

[54] MULTIPOLAR IN-LINE PROXIMAL CONNECTOR ASSEMBLY FOR AN IMPLANTABLE STIMULATION DEVICE

[75] Inventors: Edward Chernoff, Frazier Park; Harry W. Fletcher, Panorama City; Jeryle L. Walter, Newhall; James E. Barcel, Simi Valley, all of Calif.

[73] Assignee: Siemens Pacesetter, Inc., Sylmar, Calif.

[21] Appl. No.: 894,395

[22] Filed: Jun. 5, 1992

Related U.S. Application Data

[63] Continuation-in-part of Ser. No. 716,032, Jun. 14, 1991, Pat. No. 5,267,567.

[51] Int. Cl.⁵ ............................................. A61N 1/05
[52] U.S. Cl. ................................... 607/122; 607/37; 607/116; 439/669; 439/675
[58] Field of Search ............... 607/116, 122, 126, 37, 607/38; 439/909, 669, 675, 668

[56] References Cited

U.S. PATENT DOCUMENTS

| | | | |
|---|---|---|---|
| 3,641,479 | 2/1972 | O'Brien et al. | 339/94 R |
| 3,649,367 | 3/1972 | Purdy | 136/202 |
| 3,649,948 | 3/1972 | Porter | 339/16 R |
| 3,768,487 | 10/1973 | Rose | 128/419 P |
| 3,866,615 | 2/1975 | Hewson | 128/419 D |
| 4,072,154 | 2/1978 | Anderson et al. | 128/419 P |
| 4,112,953 | 9/1978 | Shanker et al. | 128/419 P |
| 4,236,525 | 12/1980 | Sluetz et al. | 128/419 P |
| 4,328,812 | 5/1982 | Ufford et al. | 128/786 |
| 4,379,462 | 4/1983 | Borkan et all. | 128/786 |
| 4,437,474 | 3/1984 | Peers-Trevarton | 128/784 |
| 4,458,695 | 7/1984 | Peers-Trevarton | 128/786 |
| 4,469,104 | 9/1984 | Peers-Trevarton | 128/419 P |
| 4,572,605 | 2/1986 | Hess | 339/177 R |
| 4,712,557 | 12/1987 | Harris | 128/419 P |
| 4,798,206 | 1/1989 | Maddison et al. | 128/419 P |
| 4,898,173 | 2/1990 | Daglow et al. | 128/419 P |
| 4,934,367 | 6/1990 | Daglow et al. | 439/527 |
| 4,944,088 | 7/1990 | Doan et al. | 29/858 |
| 4,951,687 | 8/1990 | Ufford et al. | 128/786 |
| 4,967,755 | 11/1990 | Pohndorf | 128/675 |
| 5,007,435 | 4/1991 | Doan et al. | 128/784 |
| 5,012,807 | 5/1991 | Stutz, Jr. | 128/419 P |
| 5,076,270 | 12/1991 | Stutz, Jr. | 128/419 P |

FOREIGN PATENT DOCUMENTS

| | | |
|---|---|---|
| 1589585 | 4/1970 | Fed. Rep. of Germany . |
| 1517201 | 3/1968 | France . |

OTHER PUBLICATIONS

U.S.C.I. Catheter Catalogue No. 5070105, Sec. 5, Jun. 1974 pp. 1-12.
R. McDonald, "The Design of an Implantable Cardiac Pacemaker," *Medical and Biological Engineering*, vol. 4, pp. 137-152 (Pergamon Press 1966).

*Primary Examiner*—Lee S. Cohen
*Assistant Examiner*—Brian L. Casler
*Attorney, Agent, or Firm*—Lisa P. Weinberg; Malcolm J. Romano

[57] ABSTRACT

An in-line, multipolar proximal connector assembly for an implantable stimulation lead is provided which incorporates at least one sensor. Advantageously, the present invention uses straight conductive rods, or wires, to electrically connect the proximal terminals to a multilumen lead body. The straight conductive rods enable the diameter of the lead assembly to remain small. Additional terminals can easily be added by simply decreasing the spacing between terminals and adding additional conductive rods. In one embodiment, insulating spacers are premolded to include protruding portions which interlock with the ring terminals. Recesses within the insulating spacers are dimensioned to self-position the ring terminals a precise distance from the pin terminal according to precise dimensions defined by the VS-1 (or other) standards. In another embodiment, the terminals are injection molded. While the present invention is directed towards a quadrapolar (four conductors) design, it may be easily adapted to a bipolar, tripolar or multipolar (five conductors or more) design.

7 Claims, 7 Drawing Sheets

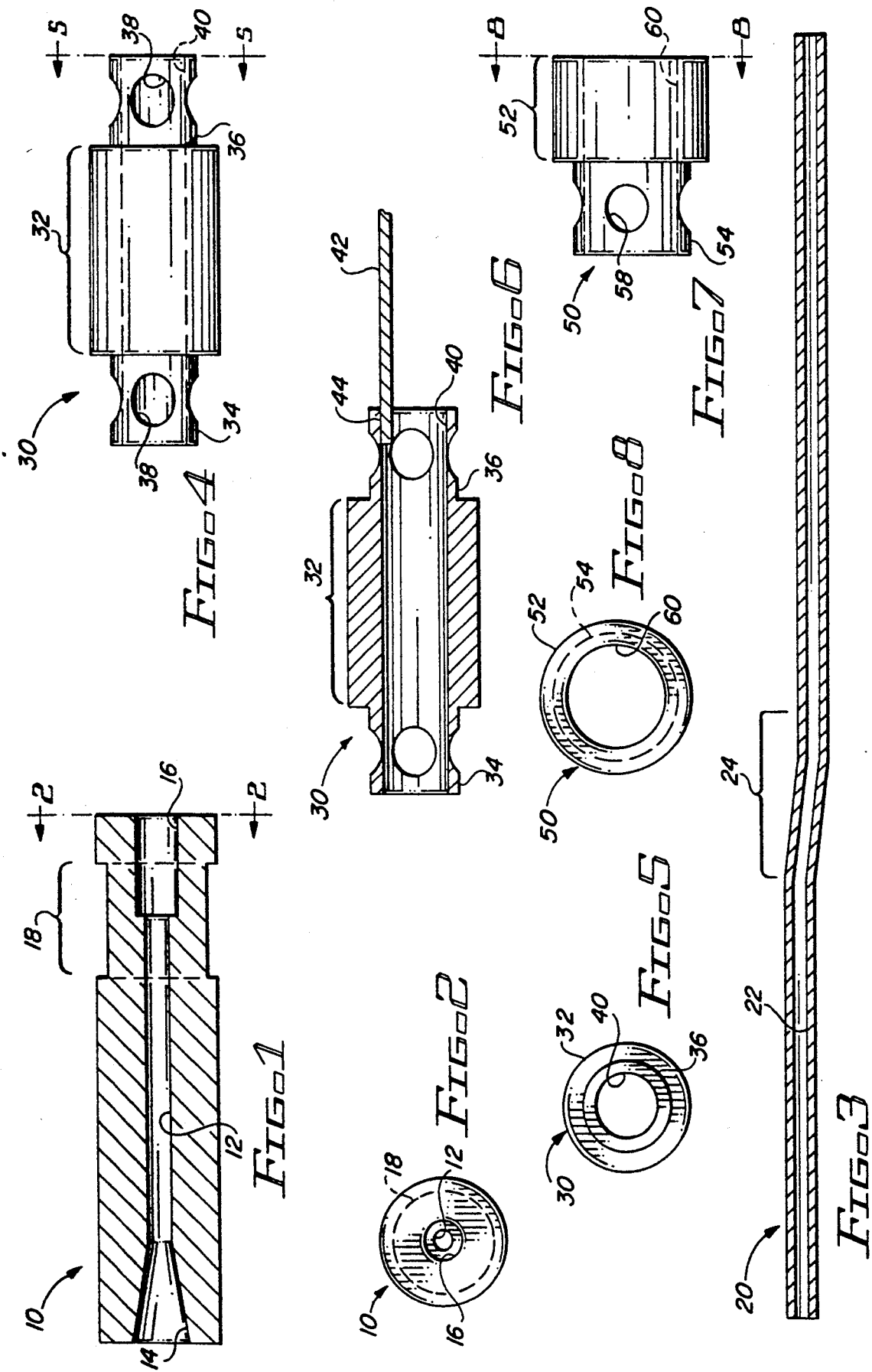

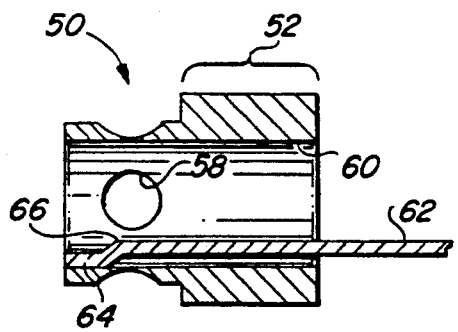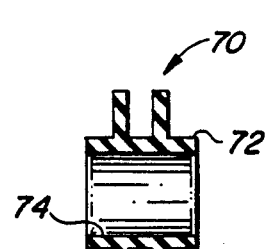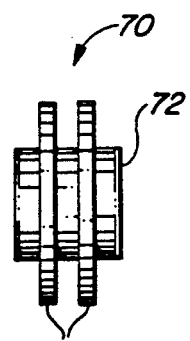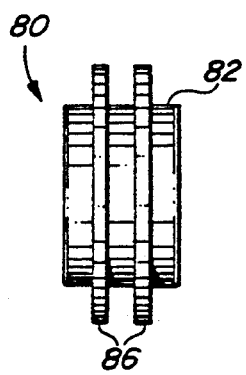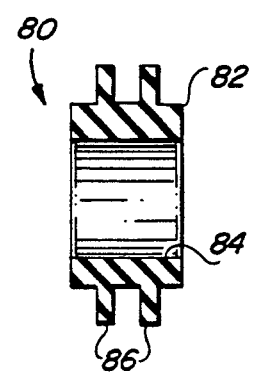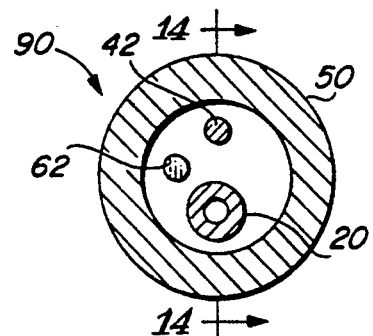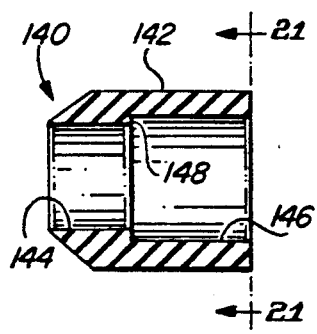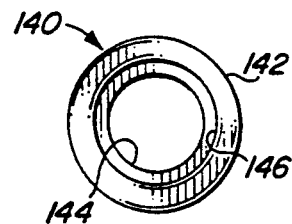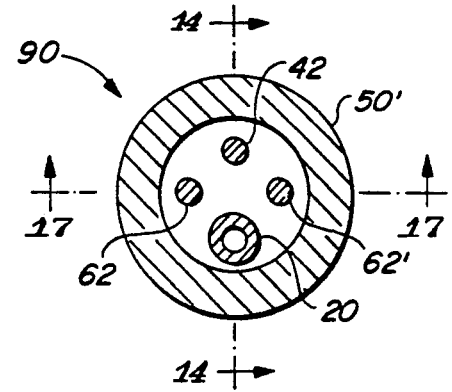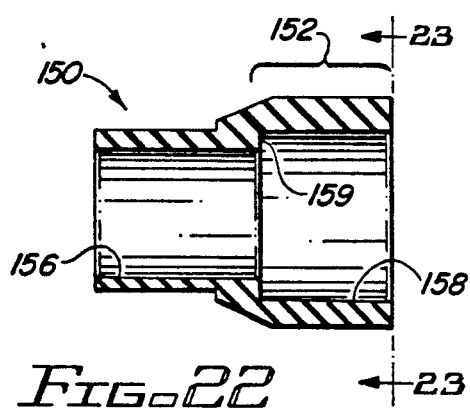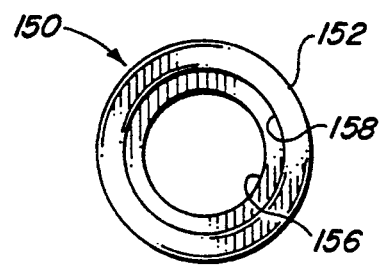

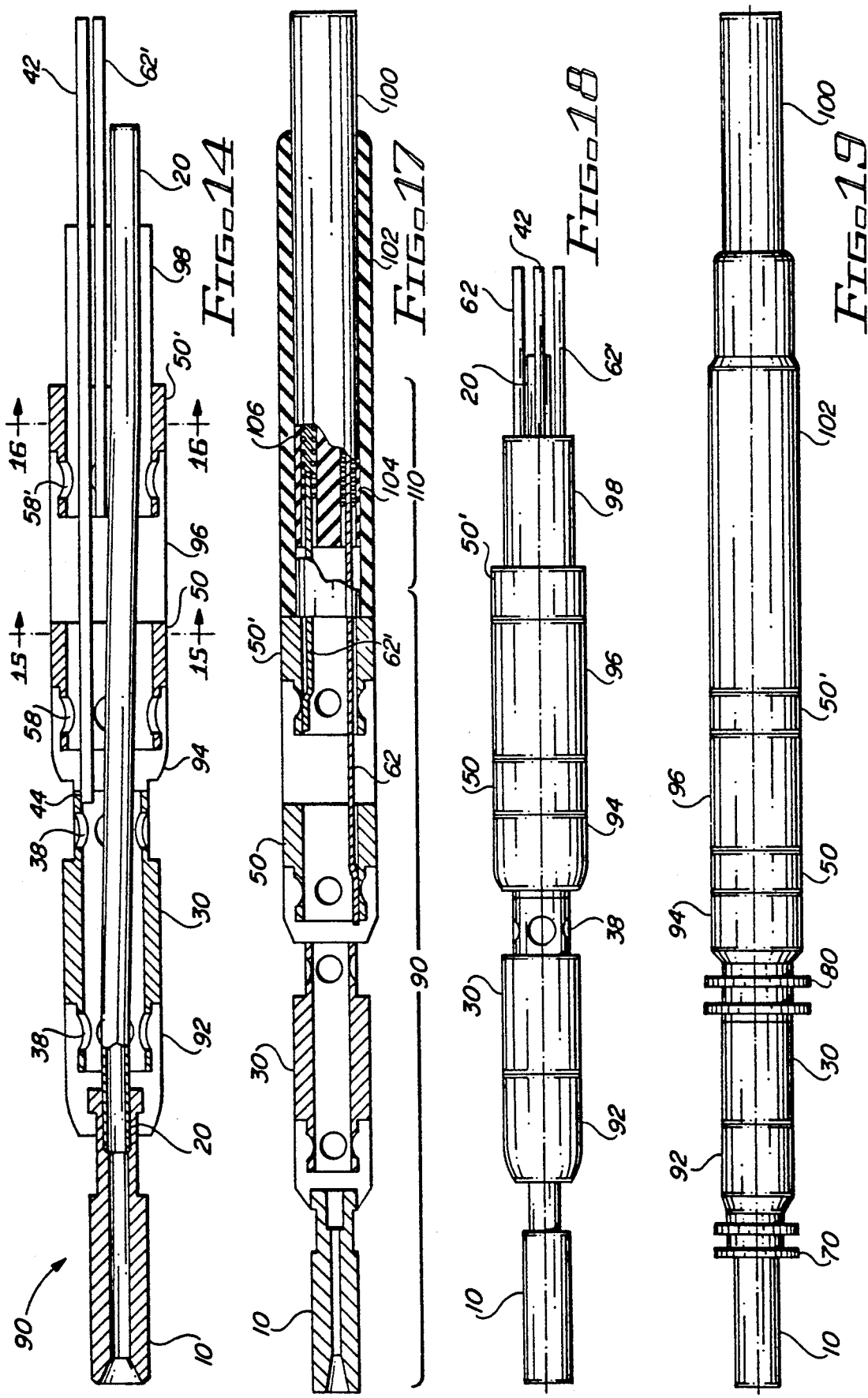

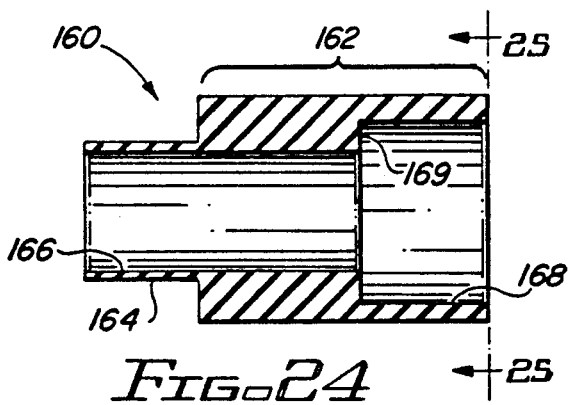
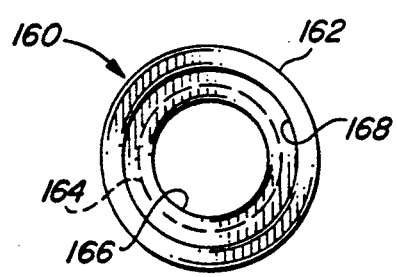
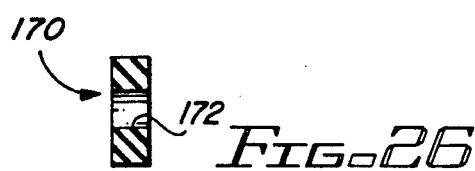
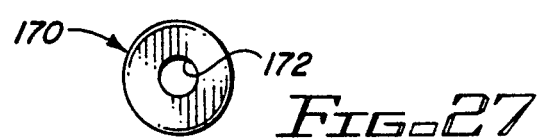
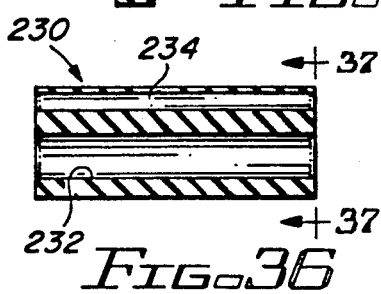
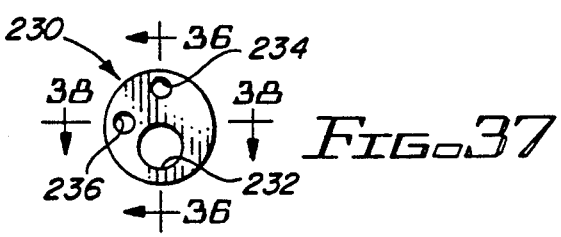
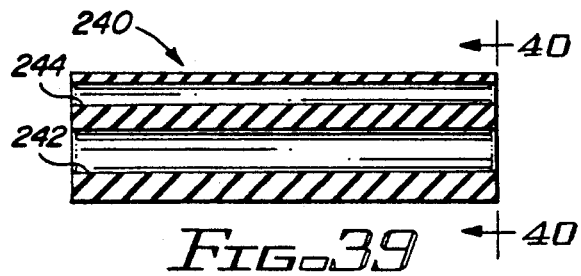
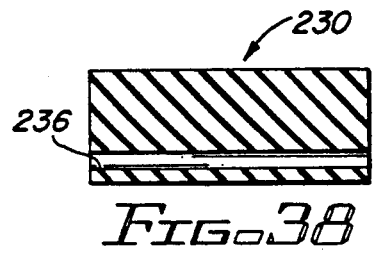
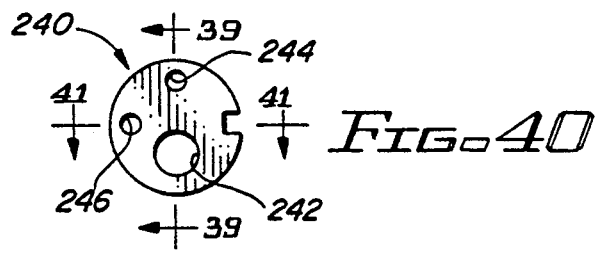
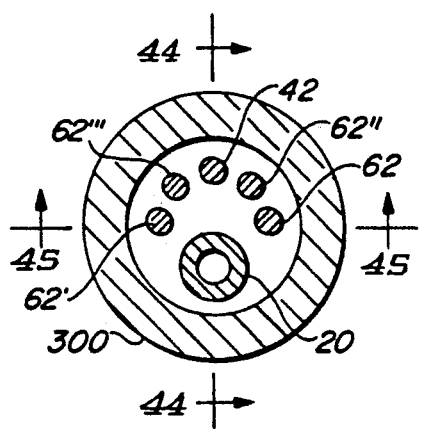
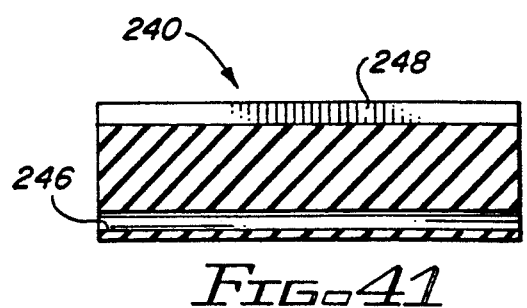

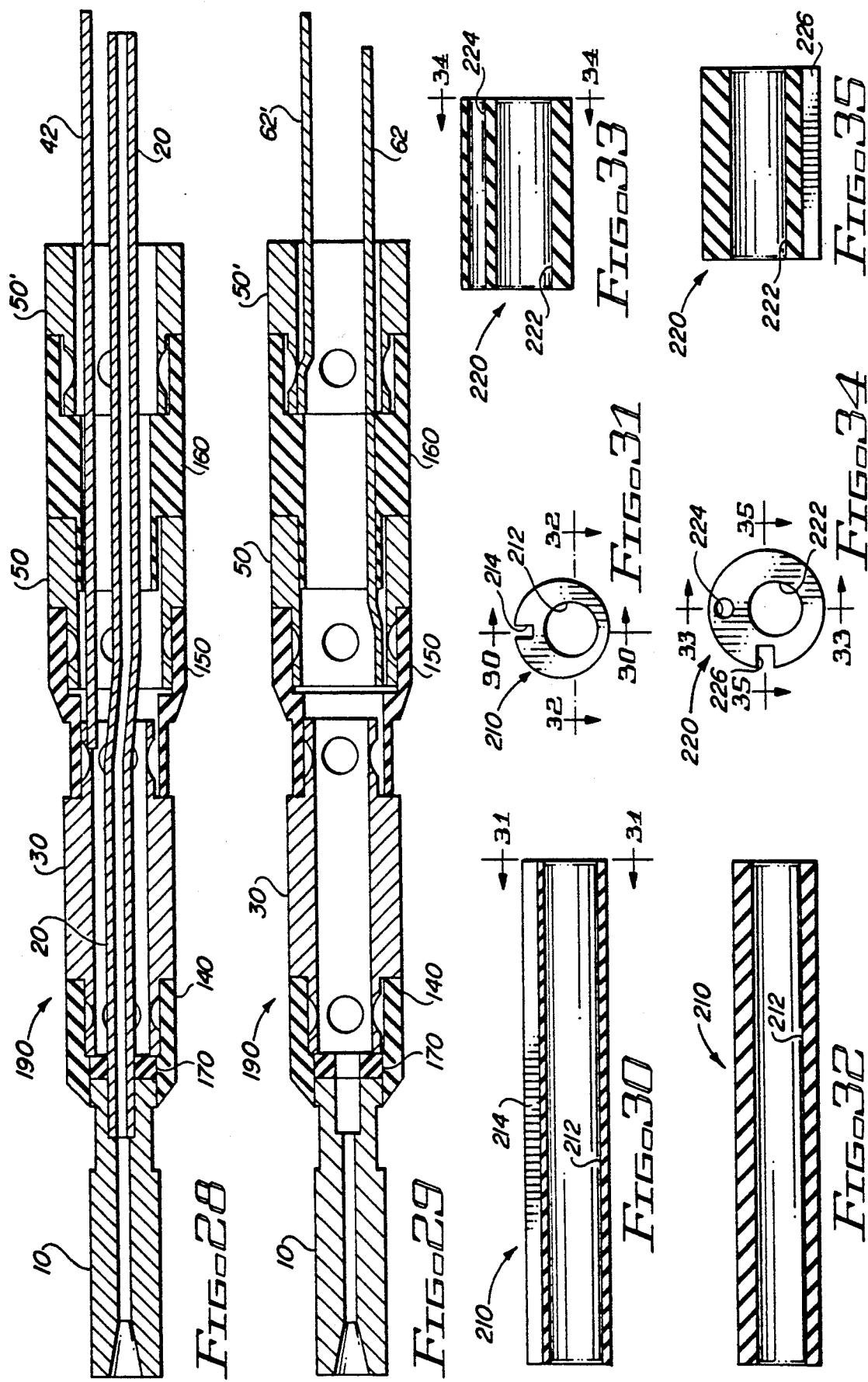

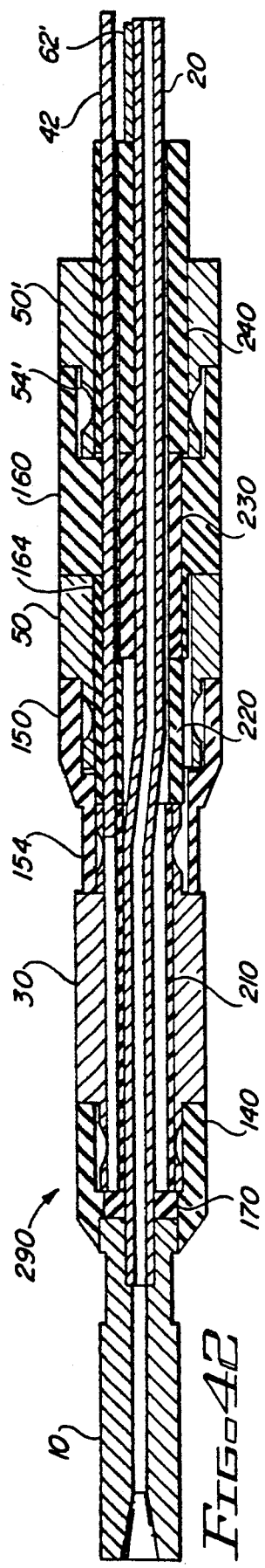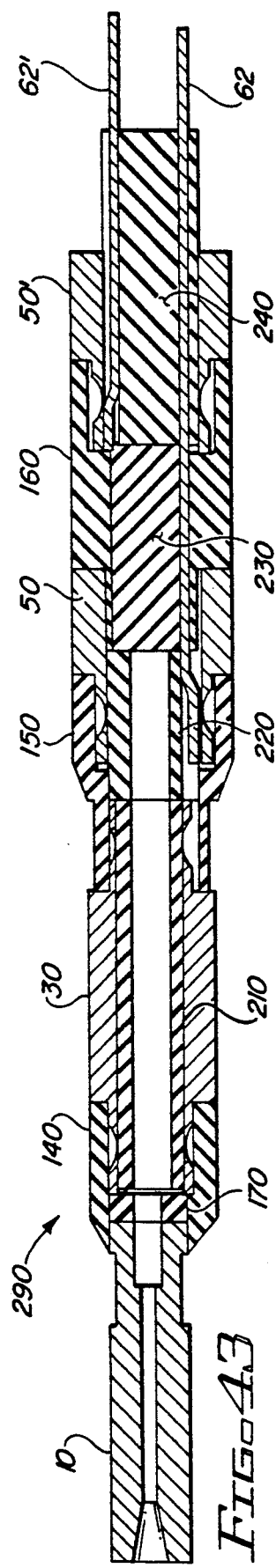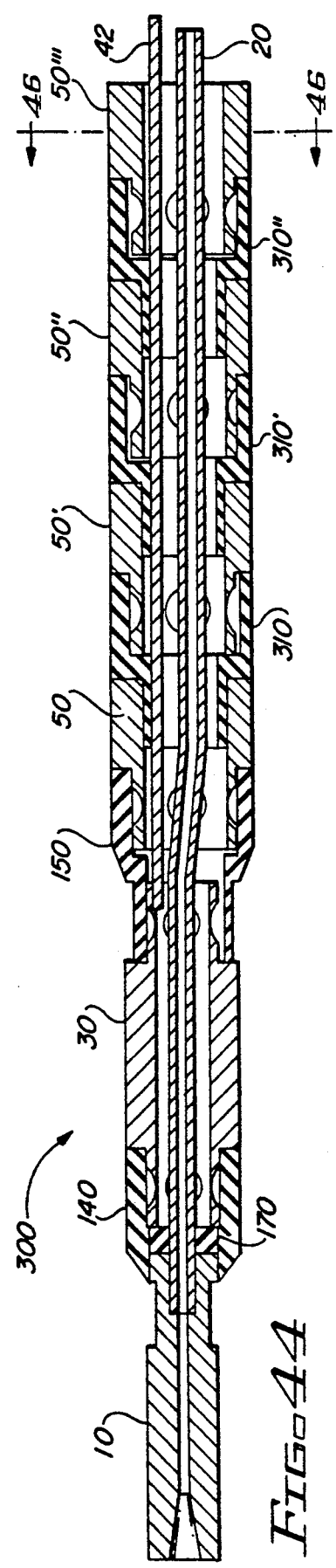

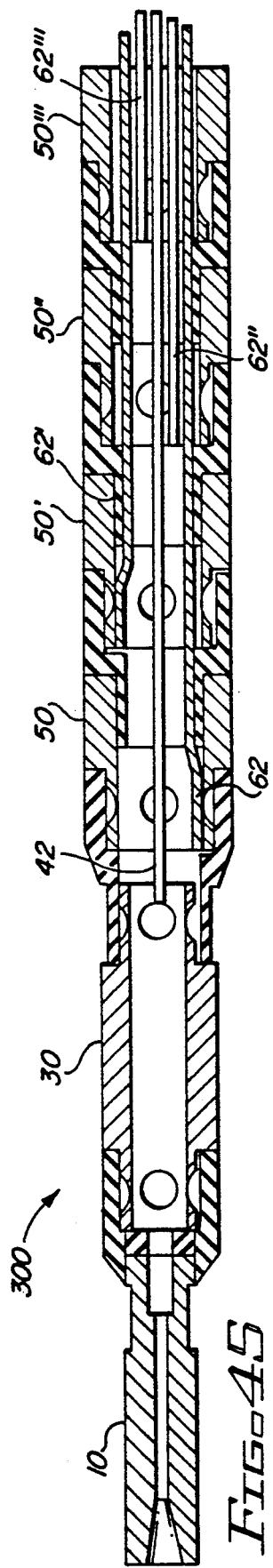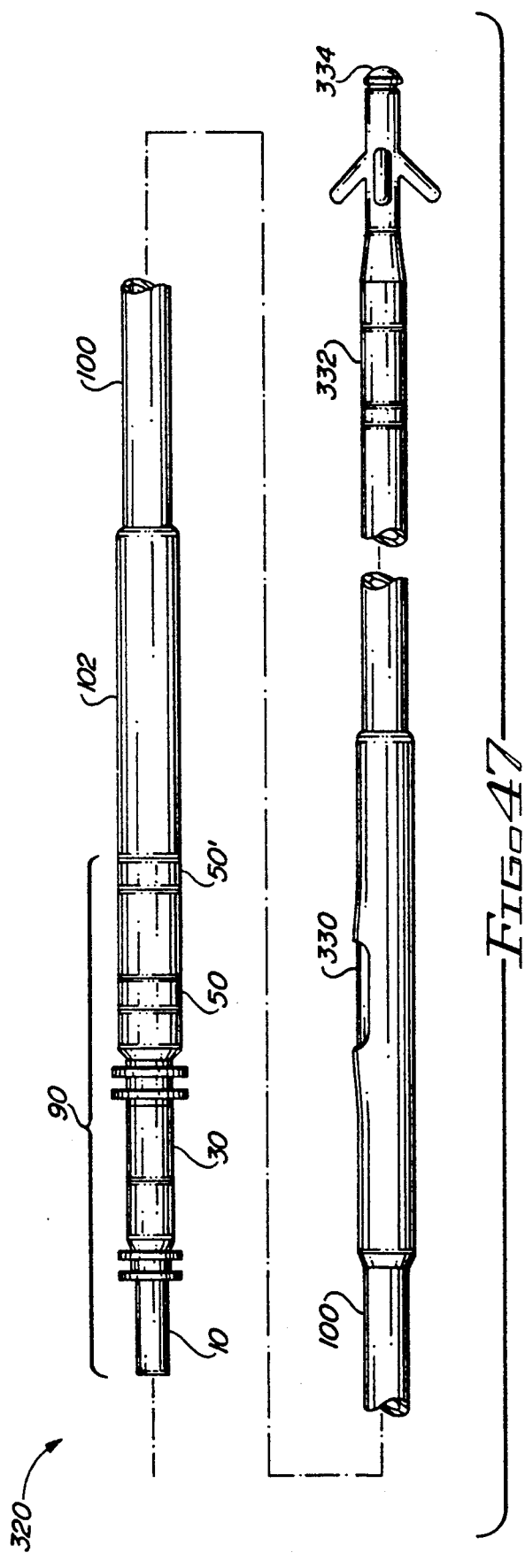

MULTIPOLAR IN-LINE PROXIMAL CONNECTOR ASSEMBLY FOR AN IMPLANTABLE STIMULATION DEVICE

CROSS-REFERENCE TO RELATED APPLICATIONS

This is a continuation-in-part of copending application Ser. No. 07/716,032, filed Jun. 14, 1991, now U.S. Pat. No. 5,267,564.

FIELD OF THE INVENTION

The present invention relates generally to implantable pacemaker leads, and more particular, to a multipolar in-line proximal connector assembly for an implantable pacemaker lead that can sense at least one physiologic parameter of the body.

BACKGROUND

An implantable stimulation lead is a medical device that delivers stimulation pulses from an implanted pulse generator to the heart, or other body tissue, for the purpose of causing a desired muscle contraction. For cardiac muscle stimulation, such lead is typically inserted through one of the main veins of the patient, e.g., the superior vena cava, so that a distal end of the lead may be directed inside the heart. Electrodes positioned at the distal end of the lead make contact with the cardiac tissue. Implantable stimulation leads may be classified as being unipolar (having a single tip electrode), bipolar (having a tip electrode and a ring electrode), or multipolar (having three or more electrodes).

As used herein, the distal end of the implantable stimulation lead is that end which makes electrical contact with the heart and the proximal end is that end which is connected to the pacemaker through a connector top. Hereinafter, the proximal end of the implantable stimulation lead will be referred to as the "proximal connector assembly". The proximal connector assembly typically takes the form of a male connector, with the pacemaker connector top taking the form of a female connector. When joined, good electrical contact must be maintained between the terminals of the proximal connector assembly and an appropriate feedthrough terminal of the pulse generator housing. Furthermore, such lead connection must be secure, so that it does not disconnect during use, yet detachable in the event the pulse generator or lead needs to be replaced. Moreover, such connections must at all times remain insulated and sealed from ionic body fluids, which body fluids are conductive and could cause an electrical short.

With the arrival of dual chambered pulse generators, it was necessary to have two female connectors within the connector top to accommodate two leads. Thus, it is preferable for bipolar leads to have an "in-line" lead assembly (as opposed to a "bifurcated" lead assembly) to minimize the height of the connector. For example, U.S. Pat. No. 4,951,687 (Ufford et al.) and U.S. Pat. No. 4,572,605 (Hess) show in-line bipolar proximal lead assemblies with and without sealing rings, respectively, made using conventional techniques. That is, these bipolar leads included a pin terminal and a ring terminal coupled to a distal tip and ring electrode, respectively, by coaxial conductors. The electrical connection to the pin terminal is made by isolating and stretching the inner coil of the coaxial conductor over the pin terminal and either crimping or welding it thereto. The electrical connection to the ring terminal is similarly made by isolating and fixturing the outer coil of the coaxial conductor onto the ring terminal and crimping or welding it thereto. Once connected the whole assembly is then injection molded in a body compatible material. However, many of the existing methods and techniques are no longer suitable for the smaller pulse generators and leads that are currently being used.

Currently, there has been a tremendous demand to incorporate physiologic sensors onto the implantable stimulation lead. These sensors will measure a variety of physiologic parameters, such as, blood oxygen saturation, blood pressure, ejection time, pH, temperature, impedance, heart wall motion, etc. The additional sensor typically requires two additional conductors and proximal terminal contacts. However, the need for additional terminal contacts also requires additional space for isolation and for enabling the crimp or weld procedure.

In anticipation of these sophisticated leads, there have been several attempts at manufacturing "tripolar" leads, that is, leads having three distal electrodes. For example, U.S. Pat. No. 4,469,104 (Peers-Trevarton) shows a lead assembly having three spaced apart metal bands with resilient conductive rings on each band adapted to make contact with a corresponding ring terminal in the connector top. U.S. Pat. No. 4,469,104 (Doan et al.) also shows, in one embodiment, a tripolar lead assembly. However, neither embodiment is easily expandable to include four or more terminals. Furthermore, each of these lead assemblies are specially designed for each manufacturer's pulse generator connector top.

Furthermore, over the approximately 30 year history of the implantable pulse generator, a wide variety of techniques and methods have been used to connect leads to pulse generators. During that time, almost no standardization existed for their dimensions. While some manufacturers strongly believed that the sealing mechanism belonged on the lead in the form of seal rings, another group preferred to have the seal rings inside the pulse generator's connector top with a smooth sealing surface located on the lead. Great variability in the actual dimensions existed even with the standard "5 mm" or "6 mm" leads available from different manufacturers. As the pulse generator electronics and batteries become smaller, the connector system represents a larger percentage of the total pulse generator volume. Thus, many manufacturers are contemplating smaller connector systems.

To avoid a proliferation of new and incompatible designs, a major effort has been underway to standardize the interface between an implantable stimulation lead and a pulse generator. The proposed voluntary standard, known as VS-1, has subsequently been adopted by almost all pulse generator manufacturers worldwide. The VS-1 standard does not specify how a particular pulse generator connector must make contact with a implantable stimulation lead, it simply defines the dimensions of the 3.2 mm implantable stimulation lead and the dimensions of the corresponding pulse generator connector cavity into which the implantable stimulation lead is inserted. The VS-1 standard further specifies certain requirements as to leakage, conductivity and connect/disconnect force. For a further explanation of the VS-1 Standard, reference is made to "A Voluntary Standard for 3.2 mm Unipolar and Bipolar Implantable Stimulation Leads and Connectors," Calfee et al., PACE, Vol. 9, 1181-85 (Nov.-Dec. 1986), which reference is hereby incorporated herein by reference.

While the VS-1 standard advantageously represents a long needed movement towards industry standardization, the VS-1 standard disadvantageously restricts the dimensions of the proximal connector assembly of the implantable lead, which can in turn limit the number of conductors and terminals.

What is needed, therefore, is a multipolar implantable stimulation lead which meets the VS-1 standard, is easy to manufacture, and can be readily expanded to include many terminals and conductors without increasing its diameter and without excessively increasing the proximal connector assembly length (which in turn would affect the pacemaker connector top dimensions). It is also an objective that all of the aforesaid advantages and objectives be achieved without incurring any substantial relative disadvantage.

SUMMARY OF THE INVENTION

It was in light of the foregoing that the present invention has been conceived and is now reduced to practice. The present invention is directed toward an in-line, quadrapolar (four electrodes) proximal connector assembly for an implantable stimulation lead which incorporates at least one sensor. In the preferred embodiment, the sensor requires electrical connection between the pacemaker and at least two (2) sensor terminals. Thus, the lead of the preferred embodiment includes four conductors, a proximal pin terminal and three proximal ring terminals corresponding to a distal tip electrode, a distal ring electrode and two sensor electrodes. The lead body comprises a body compatible tubing with at least four lumens, or holes, for insulating the four conductors.

In the proximal connector assembly of the preferred embodiment, the pin terminal is electrically connected to a conductive tube, which extends out of the distal end of the proximal connector assembly. The channel in the conductive tube serves to direct a guidewire or stylet through the proximal connector. Each of the three ring electrodes is electrically connected to a straight conductor wire which also extends out of the distal end of the proximal connector assembly. The distal ends of the conductive tube and the conductor wires are advantageously electrically connected to multifilar conductors within a multilumen lead body by splicing, welding, or other similar process. In the preferred embodiment, the pin terminal, the three ring terminals, the conductive tube and the three conductor wires are insert molded with body compatible material into a unified body. Seal rings may be molded onto the proximal connector assembly or added after the molding process.

Advantageously, the present invention uses straight conductive wires to electrically connect the proximal terminals to the conductors in the lead body. It is the use of straight rods (as opposed to coiled conductors) that enables the diameter of the lead assembly to remain small. Additional terminals can easily be added by simply decreasing the spacing between terminals and adding additional straight conductive rods.

In an alternate embodiment, the proximal connector assembly also includes a plurality of preformed insulators dimensioned so as to slidably interlock the proximal terminals. Advantageously, the preformed insulators are designed to self-position the terminals according to precise dimensions defined by the VS-1 (or other) standards. More specifically, three premolded insulating spacers include recesses dimensioned so as to prevent the ring terminals from sliding axially out of position. The length of the spacers serves to position the ring terminals a precise distance from the pin terminal.

In alternate embodiments, the present invention may be expanded to include a plurality of ring terminals so that more than two sensor connections may be incorporated into the lead. In addition, it may be readily seen that the present invention may also be employed in a standard bipolar or tripolar lead to enhance manufacturability of the proximal lead connector. In each configuration (bipolar, tripolar, quadrapolar or other multipolar), the present invention maintains the same connector diameter as the present VS-1 standard bipolar configuration.

The present invention further includes two methods of making a multipolar proximal connector assembly. Both methods include the steps of pre-attaching a pin terminal to a conductive tube, a first conductive rod to a first ring terminal, and a second conductive rod to a second ring terminal. In the preferred embodiment, the method includes insert-molding the pin terminal and the first and second ring terminals (with their respective pre-attached tubes and rods) with body compatible material to produce a unified proximal connector assembly. Additional ring electrodes (with rods pre-attached) may be easily added by shortening the distance between terminals during the molding step. In an alternate embodiment, the method includes replacing the body compatible material with premolded spacers which interjoin or interlock the terminal together.

Thus, the present invention enables a secure yet detachable connection between an implantable lead and the pacemaker connector top, while also providing greatly improved and accelerated assembly of the proximal connector assembly, increased reliability of the terminal connections, and the ability to expand to a plurality of poles maintaining the same lead diameter.

Other and further features, advantages and benefits of the invention will become apparent in the following description taken in conjunction with the following diagrams and drawings. It is to be understood that the foregoing general description and the following detailed description are exemplary and explanatory, but are not to be restrictive of the invention.

BRIEF DESCRIPTION OF THE DRAWINGS

The accompanying drawings which are incorporated in and constitute a part of this invention illustrate one of the embodiments of the invention, and together with the description serve to explain the principles of the invention in general terms.

FIG. 1 is a cross-sectional view of a pin terminal;

FIG. 2 is an end view of the pin terminal shown in FIG. 1 taken across the lines 2—2;

FIG. 3 is a cross-sectional view of a conductive tube;

FIG. 4 is a plan view of a first ring terminal;

FIG. 5 is an end view of the first ring terminal shown in FIG. 4 taken across the lines 5—5;

FIG. 6 is a cross-sectional view of the first ring terminal shown in FIG. 4 with a straight conductive wire connected thereto;

FIG. 7 is a plan view of the second (or third) ring terminal;

FIG. 8 is an end view of the second (or third) ring terminal taken across the lines 8—8;

FIG. 9 is a cross-sectional view of the second (or third) ring terminal shown in FIG. 7 with a straight conductive wire connected thereto;

FIG. 10 is a cross-sectional view of a first seal ring;

FIG. 11 is a plan view of the first seal ring shown in FIG. 10;

FIG. 12 is a plan view of a second seal ring;

FIG. 13 is a cross-sectional view of the second seal ring shown in FIG. 12;

FIG. 14 is a cross-sectional view of the MULTIPOLAR IN-LINE PROXIMAL CONNECTOR ASSEMBLY of the preferred embodiment of the present invention;

FIG. 15 is a cross-sectional view of the proximal connector assembly shown in FIG. 14 taken across the lines of 15—15;

FIG. 16 is another cross-sectional view of the proximal connector assembly shown in FIG. 14 taken across the lines of 16—16;

FIG. 17 is a cross-sectional view of the proximal connector assembly shown in FIG. 14, rotated 90 degrees and connected to a lead body and a connector boot;

FIG. 18 is a plan view of the proximal connector assembly of the present invention;

FIG. 19 is a plan view of the proximal connector assembly of the present invention connected to a lead body and a connector boot;

FIG. 20 is a cross-sectional view of a first premolded insulating spacer;

FIG. 21 is an end view of the first premolded insulating spacer shown in FIG. 20 taken across the lines of 21—21;

FIG. 22 is a cross-sectional view of a second premolded insulating spacer;

FIG. 23 is an end view of the second premolded insulating spacer shown in FIG. 22 taken across the lines of 23—23;

FIG. 24 is a cross-sectional view of a third premolded insulating spacer;

FIG. 25 is an end view of the third premolded insulating spacer shown in FIG. 24 taken across the lines of 25—25;

FIG. 26 is a cross-sectional view of a fourth premolded insulating spacer;

FIG. 27 is an end view of the fourth premolded insulating spacer shown in FIG. 26;

FIG. 28 is a second embodiment of the multipolar in-line proximal connector assembly using the first, second and third insulating spacers shown in FIGS. 20-27;

FIG. 29 is a cross-sectional view of the proximal connector assembly shown in FIG. 28, rotated 90 degrees;

FIG. 30 is a cross-sectional view of a first insulating tube;

FIG. 31 is an end view of the first insulating tube shown in FIG. 30 taken along the lines of 31—31;

FIG. 32 is another cross-sectional view of the first insulating tube shown in FIG. 31 taken along the lines of 32—32;

FIG. 33 is a cross-sectional view of a second insulating tube;

FIG. 34 is an end view of the second insulating tube shown in FIG. 33 taken along the lines of 33—33;

FIG. 35 is another cross-sectional view of the second insulating tube shown in FIG. 34 taken along the lines of 35—35;

FIG. 36 is a cross-sectional view of a third insulating tube;

FIG. 37 is an end view of the third insulating tube shown in FIG. 36 taken along the lines of 37—37;

FIG. 38 is another cross-sectional view of the third insulating tube shown in FIG. 36 taken along the lines of 38—38;

FIG. 39 is a cross-sectional view of a fourth insulating tube;

FIG. 40 is an end view of the fourth insulating tube shown in FIG. 39 taken along the lines of 40—40;

FIG. 41 is another cross-sectional view of the fourth insulating tube shown in FIG. 40 taken along the lines of 41—41;

FIG. 42 is a third embodiment of the multipolar in-line proximal connector assembly using the insulating spacers and the insulating tubes shown in FIGS. 20-27 and 30-31, respectively;

FIG. 43 is a cross-sectional view of the proximal connector assembly shown in FIG. 42, rotated 90 degrees;

FIG. 44 is a cross-sectional view of multipolar in-line proximal connector assembly which includes 5 ring terminals;

FIG. 45 is a cross-sectional view of the proximal connector assembly shown in FIG. 44, rotated 90 degrees;

FIG. 46 is a cross-sectional view of the proximal connector assembly shown in FIG. 44 taken along the lines of 46—46; and FIG. 47 is a side view of the body implantable lead of the present invention with a sensor mounted therein.

DESCRIPTION OF THE PREFERRED EMBODIMENTS

The following description is of the best mode presently contemplated for practicing the invention. This description is not to be taken in a limiting sense, but is made merely for the purpose of describing the general principles of the invention. The scope of the invention should be ascertained with reference to the issued claims. In the description of the invention that follows, like numerals or reference designators will be used to refer to like parts or elements throughout.

While the present invention was conceived during the development of a multipolar proximal connector assembly for an oxygen saturation sensing lead, it is to be understood that the present invention could be used with any remote sensor located on an implantable lead. Since oxygen saturation sensors have typically required two additional conductors, the present invention is directed toward a quadrapolar (four conductors) proximal connector assembly. For a complete description of an oxygen saturation lead, reference is made to copending U.S. patent application Ser. No. 07/716,032, entitled "Pacemaker Lead for Sensing a Physiologic Parameter of the Body," filed 6/14/91, which application is hereby incorporated herein by reference.

FIGS. 1 and 2 show a detailed cross-sectional view and an end view of a pin terminal 10. The pin terminal 10 has a channel 12 through which a guidewire or stylet may be passed during implantation. To facilitate the insertion of the guide wire, the channel 12 has a flanged end 14. The pin terminal 10 has a recess 16 at the other end dimensioned to receive a conductive tube (not shown). The pin terminal 10 also has a narrow neck portion 18 where the pin terminal 10 is designed to have seal rings (not shown) attached or molded thereon. It is understood that the narrow neck area 18 may include some type of gripping means, such as ridges or grooves, to help adhere the seal rings to the pin terminal 10.

In FIG. 3, a cross-sectional view of a conductive tube 20 is shown to include a channel 22 extending therethrough for passing the guide wire or stylet. The outer diameter of the channel 20 is dimensioned to be slidably inserted within the recess 16 (FIG. 1) of the pin terminal 10. The conductive tube has a slight bend in the area of 24, the purpose of which will be described in conjunction with other Figures.

In FIGS. 4, 5 and 6, a first ring terminal 30, made of conductive material, is shown having a main body 32 (which provides a large contact area for connection to the pacemaker receptacle) and a first and second protruding portions 34, 36, respectively, at either end. A plurality of holes 38 located around the first and second protruding portions 34, 36 are used to grip silicone rubber, or other adhesives, used to bond the final assembly together. Extending through the first ring terminal 30 is a channel 40 (FIG. 6). In FIG. 6, a conductive wire 42 is also shown attached to the first ring terminal 30 at location 44 of the channel 40.

FIGS. 7, 8 and 9 show a plan, end and cross-sectional view, respectively, of a second ring terminal 50. The second ring terminal is shown having a main body 52 which provides a large electrode surface area for contact with bodily fluids. In the preferred embodiment, the main body 52 is approximately ⅓ the length of the main body 32 of the first ring terminal 30. However, it is also recognized that the length of the second (and other additional) ring terminals can be made even smaller to accommodate a plurality of terminals in the same proximal connector assembly and is limited only by the pacemaker connector technology. The length of the main body 52 is currently designed to align with a standard garter spring connector, as is known in the art.

The second ring terminal 50 also includes a protruding portion 54 at one end. A plurality of holes 58 located around the first protruding portion 54 is used to grip silicone rubber, or other adhesive, which is used to bond the final assembly together. Extending through the second ring terminal 50 is a channel 60. In FIG. 9, a conductive wire 62 is also shown attached to the second ring terminal 50 at location 64 of the channel 60. A distal end 66 of the conductive wire 62 is bent slightly and welded, or otherwise attached, to the second ring electrode 50.

In the preferred embodiment, the third ring terminal is identical to the second ring terminal 50. To distinguish the third ring terminal, a prime (') will be used for corresponding elements, e.g., a third ring terminal 50' includes a main body 52' having a protruding portion 54' with a plurality of holes 58', etc.

In the preferred embodiment, two seal rings are used on each proximal connector assembly. A first seal ring 70, shown in FIGS. 10 and 11, has a main body 72 with a channel 74 dimensioned to fit around the narrow neck portion 18 of the pin terminal 10. Two o-rings 76 are dimensioned to form a tight seal within the pacemaker connector top. Thus, the first seal ring 70 prevents bodily fluids from creating a low impedance leakage pathway between the pin terminal and the ring electrode.

A second seal ring 80, shown in FIGS. 12 and 13, has a main body 82 with a channel 84 dimensioned to fit around the one of the protruding portions of the first ring terminal, either 34 or 36, which ever is most distal from the pin terminal. Two o-rings 86 are dimensioned to form a tight seal within the pacemaker connector top. Thus, the second seal ring 80 provides a second barrier against bodily fluids.

In conjunction with FIGS. 14, 15, 16 and 17, the method of assembly will now be described. In the preferred embodiment, the conductive tube 20 is slid into the recess 16 of pin terminal 10 and welded, or otherwise electrically attached, thereto. The first ring terminal 30, with the conductive wire 42 pre-attached, is then slid over the conductive tube 20. Next, the second ring terminal 50, with the conductive wire 62 (not shown) pre-attached, is slid over the conductive tube 20. Likewise, the third ring terminal 50', with the conductive wire 62' pre-attached, is slid over the conductive tube 20. The terminals (10, 30, 50 and 50'), the conductive tube 20 and the conductive wires (42, 62 and 62') are then placed in a precision mold and injected with body compatible material to produce the proximal connector assembly shown in FIG. 14. Suitable materials include the polyurethane material sold under the trademark PELLATHANE and manufactured by Dow, or an elastomer material manufactured by Dow Corning, such as Elastomer #Q7-4765, or equivalent type of silicone rubber. The body compatible material flows into the holes 38, 58 and 58' in the ring terminals 30, 50 and 50', respectively, which improves the mechanical strength and the bonding between the body compatible material and the terminals. The body compatible material also flows into molded portions 92, 94, 96 and 98.

Advantageously, conductive wires 42, 62 and 62' are straight wires made of a resilient, noncorroding metal, preferably MP35N alloy. This configuration thereby eliminates unnecessary bulk in the multipolar proximal connector assembly 90. Preferably, each of the conductor wires 42, 62 and 62' is electrically insulated from each by a thin polymer insulative coating. The insulative coating may be one of the polymer materials sold under the trademarks TEFLON and TEFZEL, manufactured by DuPont, which materials have good electrical insulating properties without adding significant bulk.

In the preferred embodiment, the conductive tube 20, together with the first, second and third ring terminals 30, 50 and 50', enable a stiffer body construction so that the conductive wires 42, 62 and 62' are not subject to excessive stresses which would cause fatigue and breakages. In FIGS. 14 and 17, the proximal connector assembly is shown prior to attachment of the first and second seal rings 70 and 80.

FIG. 17 further shows the proximal connector assembly 90 connected to a multilumen lead body 100 and a connector boot 102. In this partial cross-sectional view, the conductive wires 62 and 62, are clearly seen extending out of the distal end of the proximal connector assembly 90. The multilumen lead body 100 has four coiled conductors which are dimensioned to receive the conductive wires 42, 62, 62' and the conductive tube 20, respectively, therein. While FIG. 17 only shows two of the four conductors (104 and 106), each of the conductors is attached to the proximal connector assembly 90 in similar fashion. For example, conductive wire 62 is advantageously dimensioned to be slidably inserted within the coiled conductor 104 and then welded, crimped, or otherwise electrically attached thereto. The multilumen lead body 100 is then slid over the spliced area 110.

The connector boot 102 may be attached in a variety of ways. For example, the connector boot 102 may be preformed, stretched and then slid over the spliced area 110 to provide additional stiffness and protection against fatigue and breakages. Alternately, the connector boot 102 may be expanded by soaking it in a solvent such as isopropyl alcohol or the material sold under the trademark FREON and manufactured by Dupont.

FIGS. 18 and 19 are simply plan views of the proximal connector assembly 90 corresponding to FIGS. 14 and 17, respectively. In FIG. 19, the first and second seal rings 70, 80 are also shown attached, which attachment may be accomplished in a variety of ways. For example, the seal rings 70, 80 may be preformed, stretched and then slid into place. Alternately, the seal rings 70, 80 may be expanded by soaking them in a solvent such as isopropyl alcohol or the material sold under the trademark FREON and manufactured by Dupont, and then slid into place. In another embodiment, the seal rings 70, 80 may be insert molded together with the pin terminal 10 and the first, second and third ring terminals 30, 50, 50'. Seal rings could also be placed between electrical contacts 50 and 50', and between electrical contact 50' and the body. However, in the preferred embodiment, these seal rings are located within a pacemaker's connector top.

In an alternate embodiment, the injection molded portions of the proximal connector assembly 90 are replaced by a plurality of premolded insulating spacers which are dimensioned to self-position each of the terminals a precise distance from each other. More specifically, the injection molded portions 92, 94 and 96 shown in FIG. 18 may be replaced with a first, a second, and a third premolded insulating spacer 140, 150 and 160, as shown in FIGS. 20-21, 22-23, 24-25, respectively.

As shown in FIGS. 20-21, the first insulating spacer 140 includes a main body 142 with a first recess 144 for receiving the one end of the pin terminal 10. The first insulating spacer 140 further includes a second recess 146 for receiving the first protruding portion 34 of the first ring terminal 30.

In FIGS. 22-23, the second insulating spacer 150 includes a main body 152 and a protruding portion 154. The protruding portion 154 has a recess 156 therein for receiving the second protruding portion 36 of the first ring terminal 30. The main body 152 includes a recess 158 for receiving the protruding portion 54 of the second ring terminal 50.

In FIGS. 24-25, the third insulating spacer 160 includes a main body 162 and a protruding portion 164. The third insulating spacer 160 includes a channel 166 for passing the conductive wires 42, 62 and the conductive tube 20 therethrough. The outer diameter of the protruding portion 164 is, advantageously, dimensioned to fit within the channel 60 of the second ring terminal 50. The main body 162 includes a recess 168 dimensioned to receive the protruding portion 54' of the third ring terminal 50'.

In the preferred embodiment, a fourth insulating spacer 170 (shown in FIGS. 26 and 27) is inserted within the first insulating spacer to insulate and self-position the pin terminal 10 a precise distance from the first ring terminal 30. The fourth insulating spacer includes a channel 172 for passing the conductive tube 20. However, it is recognized that the fourth insulating spacer 170 could be integrally formed in the first insulation spacer 140.

The proximal connector assembly 190, which employs the plurality premolded insulating spacers 140, 150 and 160, is shown in FIGS. 28 and 29. FIG. 28 is a cross-sectional view corresponding to the view shown in FIG. 14 of the preferred embodiment. FIG. 29 is a cross-sectional view rotated 90 degrees, with the conductive tube omitted for clarity.

In one embodiment, the proximal connector assembly 190 is injection molded with body compatible material, such as silicone rubber, in the inner cavity where the conductive tube 20, the conductive wires 42, 62, and 62' reside, thus, insulating them from each other. In addition, the conductive wires would preferably have a thin insulative outer coating, such as the polymer materials sold under the trademarks TEFLON and TEFZEL, manufactured by DuPont, which materials have good electrical insulating properties without adding significant bulk.

In another embodiment, a plurality of premolded insulating tubes are used to fill and electrically isolate the conductive tube 20 and the conductive wires 42, 62, and 62' from each other. A first insulating tube 210 is shown in FIGS. 30-41.

The first insulating tube 210 has a main channel 212 and a slot 214, as shown in FIGS. 30-32. The slot 214 is dimensioned to slidably fit the conductive wire 42 therein so that the conductive wire 42 may make electrical contact with the first ring terminal 30. The main channel 212 is dimensioned to slidably fit the conductive tube 20 therein. The outer diameter of the first insulating tube 210 is dimensioned to slidably fit within the first ring terminal 30.

FIGS. 33-35 show a second insulating tube 220 having a main channel 222, a channel 224 and a slot 226. The main channel 222 is dimensioned to receive the conductive tube 20 therein. The channel 224 is dimensioned to pass the conductive wire 42 therethrough. The slot 226 is dimensioned to slidably fit the conductive wire 62 therein so that the conductive wire 62 may make electrical contact with the second ring terminal 50. The outer diameter of the second insulating tube 220 is dimensioned to slidably fit within the second ring terminal 50.

FIGS. 36-38 show a third insulating tube 230 having a main channel 232, a first channel 234 and a second channel 236. The main channel 232 is dimensioned to receive the conductive tube 20 therein. The first channel 234 is dimensioned to pass the conductive wire 42 therethrough. The second channel 236 is dimensioned to slidably pass the conductive wire 62 therethrough. Since the third insulating tube 230 does not have to accommodate the bent shape of the conductive tube, the main channel 232 is smaller than the main channel 222 of the second insulating tube 220. The bend in the conductive tube thereby enables more uniform spacing between the conductive wires 42, 62, and 62' at the distal end of the proximal connector assembly 190. The outer diameter of the third insulating tube 230 is dimensioned to slidably fit within the main channel 166 of the third insulating spacer 160.

FIGS. 39-41 show a fourth insulating tube 240 having a main channel 242, a first channel 244, a second channel 246 and a slot 248. The main channel 242 is dimensioned to receive the conductive tube 20 therein. The first channel 244 is dimensioned to pass the conductive wire 42 therethrough. The second channel 246 is dimensioned to pass the conductive wire 62 therethrough. The slot 248 is dimensioned to slidably fit the conductive wire 62' therein so that the conductive wire 62' may make electrical contact with the second ring terminal 50'. The outer diameter of the fourth insulating tube 240 is dimensioned to slidably fit within the third ring terminal 50'.

The proximal connector assembly 290, which employs the premolded insulating spacers 140, 150 and 160 and the premolded insulating tubes 210, 220, 230 and 240, is shown in FIGS. 42 and 43. FIG. 42 is a cross-sectional view corresponding to the view shown in FIG. 28. FIG. 43 is a cross-sectional view rotated 90 degrees, with the conductive tube omitted for clarity.

With respect to FIGS. 42 and 43, the preferred method of this alternate embodiment will now be described. First, the conductive tube 20 is welded or otherwise electrically attached to the distal end of the pin terminal 10. Likewise, the conductive wires 42, 62 and 62' are welded or otherwise electrically attached to the first, second and third ring terminals 30, 50 and 50', respectively.

Next, the fourth insulating spacer 170 is slid over the conductive tube 20 and adhesively attached to the distal end of the pin terminal 10. The distal end of the pin terminal 10 is then slidably inserted within the first recess 144 of the first insulating spacer 140. The first protruding portion 34 of the first ring terminal 30 is next slid within the second recess 146 of the first insulating spacer 140. Advantageously, a shoulder 148 (FIG. 20) prevents the first ring terminal 30 from sliding axially too far into the first insulating spacer 140. The fourth insulating spacer 170 creates a precise distance between the first ring terminal 30 and the pin terminal 10.

Next, the first insulating tube 210 is slid over the conductive tube 20 with the conductive wire 42 extending through the slot 214 so that it may make electrical contact with the first ring terminal 30. The protruding portion 154 of the second insulating spacer 150 is then slid over the second protruding portion 36 of the first ring terminal 30. The protruding portion 54 of the second ring terminal 50 is slidably inserted within the recess 158 until it butts up against a shoulder 159 (FIG. 22). Insulating tube 220 is then slidably inserted within the second ring terminal 50 so that the conductive tube 30 and the conductive wire 42 pass therethrough.

The protruding portion 164 of the third insulating spacer 160 is dimensioned to be slidably inserted within the channel 60 of the second ring terminal 50. The third insulating tube 230 is slidably inserted within the third insulating spacer 160 so that the conductive tube 30 and conductive wires 42 and 62 pass therethrough.

The protruding portion 54' of the third ring terminal 50' is slidably inserted within the recess 168 until is butts up against a shoulder 169 (FIG. 24). Insulating tube 240 is then slidably inserted within the third ring terminal 50' so that the conductive tube 30 and the conductive wires 42, 62 and 62' pass therethrough. Epoxy, or other suitable adhesive, may be used between adjacent insulating spacers to bond the assembly together. The assembly is then over-molded in silicone rubber, or other body compatible material.

A side view of the implantable pacemaker lead 320 is shown in FIG. 47. The pacemaker lead 320 includes a multipolar connector assembly 90 having the pin terminal 10 and three ring terminals 30, 50 and 50'. The pacemaker lead 320 further includes the multilumen lead body 100, the connector boot 102, a sensor 330, a ring electrode 332 and a tip electrode 334. The pin terminal 10 is connected to the tip electrode 334. The ring terminal 30 is connected to the ring electrode 332. The second and third ring terminals 50, 50' are connected to a first and second sensor terminal (not shown), respectively. For a complete description of mounting and making electrical connections to the sensor 330 and lead 320, reference is made to copending U.S. patent application Ser. No. 07/716,032, entitled "Pacemaker Lead for Sensing a Physiologic Parameter of the Body," filed 6/14/91, which application is hereby incorporated herein by reference. As is known in the art, sensing cardiac events occurs using the same electrodes as for stimulation (i.e., terminals 332 and 334).

The present invention differs from the prior art in that the present invention does not use multiconductor coils in the proximal connector assembly. In the prior art, multiconductor coils offer the advantages of redundancy and flexibility. However, their overall diameter severely limits the number of conductors one can use in a multipolar proximal connector assembly. The present invention combines straight conductive rods and a stiffer body construction to eliminate any concerns about breaking the electrical connection. Thus, it can be seen that a plurality of conductive rods and ring electrodes may be added to the multipolar proximal connector assembly without increasing the overall diameter. Furthermore, it can be seen that the present invention could be used in a bipolar configuration to simplify lead assembly and may be expandable to a plurality of ring terminals.

Advantageously, each of the insulating spacers 140, 150, 160, 170 and insulating tubes 210, 220, 230 and 240 are premolded using polysulfone, polyether sulfone, or an equivalent class 6 polymer insulating material. The premolded components offer the advantages of rapid assembly, self-positioning of electrodes, precise dimensions, and ease of handling.

In FIGS. 44-46, the proximal connector assembly 300 includes a pin terminal 10, a first ring terminal 30, and four additional identical sensor terminals 50, 50', 50" and 50'''. Notice that insulating spacers 310, 310' and 310" are simply a modified insulating spacer 160 with a shorter main body 162 to permit more sensor terminals in the same amount of space.

Thus, it may be apparent that the proximal connector assembly of the present invention consists of a plurality of terminals with straight conductive rods or wires, thus enabling an expandable proximal connector assembly with an extremely slim profile. Furthermore, the preferred embodiment of the present invention includes a plurality of insulating spacers which enable easy and rapid assembly by an operator. By virtue of the shoulders on the insulating spacers, each of the ring terminals is self-positioned with respect to the pin terminal.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An implantable stimulation lead having a proximal end and a distal end having at least tip and ring electrodes and a sensor for sensing a physiological parameter of the body, the sensor having a first and second sensor terminal, the tip and ring electrodes and the first and second sensor terminals being coupled to at least a first, a second, a third and a fourth conductor, respectively, the implantable stimulation lead further comprising:

a pin terminal at the proximal end;

at least a first, second and third ring terminal at its proximal end;

at least a first, second and third conductive rod, each rod having a proximal end in electrical contact with only one of the ring terminals without touching the other of the ring terminals, each rod having a distal end electrically connected to a respective one of the second, third and fourth conductors;

a conductive tube electrically connected to the pin terminal, the conductive tube being shaped to avoid electrical contact with the ring terminals and their respective rods, the conductive tube being electrically connected to the first conductor; and a plurality of prefabricated insulating spacers, each spacer having mechanical joining means for slidably joining, while electrically insulating, one pair of adjacent proximal terminals;

whereby the sensor is electrically connected between the second and third ring terminals and electrically isolated from the tip and ring electrodes.

2. The implantable stimulation lead, as recited in claim 1, wherein:

the plurality of prefabricated insulating spacers have a predetermined width for axially positioning each of the respective pairs of adjacent proximal terminals a prescribed distance.

3. The implantable stimulation lead, as recited in claim 2, wherein the plurality of prefabricated insulating spacers comprise:

a first prefabricated insulating spacer axially positioning the pin terminal a first prescribed distance from the first ring terminal;

a second prefabricated insulating spacer axially positioning the first ring terminal a prescribed distance from the second ring terminal; and a third prefabricated insulating spacer axially positioning the second ring terminal a prescribed distance from the third ring terminal.

4. The implantable stimulation lead, as recited in claim 1, wherein the plurality of insulating spacers further comprise:

a plurality of inner insulating spacers, slidable over the conductive tube, insulating each of the ring terminals and their respective rods from the conductive tube.

5. The implantable stimulation lead, as recited in claim 1, further comprising:

a liquified biocompatible material placed around the conductive tube and within a channel formed by the ring terminals and the plurality of prefabricated insulating spacers so that the ring terminals and their respective rods are insulated from the conductive tube.

6. An implantable stimulation lead having at least distal tip and ring electrodes and a sensor for sensing a physiological parameter of the body, the sensor having a first and second sensor terminal, the tip and ring electrodes and the first and second sensor terminals being coupled to at least a first, a second, a third and a fourth conductor, respectively, the implantable stimulation lead further comprising:

a pin terminal;

at least a first, second and third ring terminal;

at least a first, second and third conductive rod, each rod having a proximal end in electrical contact with only one of the ring terminals without touching the other of the ring terminals, each rod having a distal end electrically connected to a respective one of the second, third and fourth conductors;

a conductive tube electrically connected to the pin terminal, the conductive tube being shaped to avoid electrical contact with the ring terminals and their respective rods, the conductive tube being electrically connected to the first conductor; and insulating means for providing electrical isolation between each of the pin, the first, the second and the third ring terminals;

whereby the sensor is electrically connected between the second and third ring terminals and electrically isolated from the tip and ring electrodes.

7. The implantable stimulation lead, as recited in claim 6, wherein:

the insulating means comprises injection molded biocompatible material.

* * * * *

UNITED STATES PATENT AND TRADEMARK OFFICE
CERTIFICATE OF CORRECTION

PATENT NO. : 5,304,219
DATED : April 19, 1994
INVENTOR(S) : Edward Chernoff et al.

It is certified that error appears in the above-indentified patent and that said Letters Patent is hereby corrected as shown below:

Column 1, line 1 and
On the coverpage, section [54], delete the title "Multipolar In-Line Proximal Connector Assembly for an Implantable Stimulation Device", and insert therefor --An Implantable Stimulation Lead Having a Multipolar In-Line Proximal Assembly--.

On the cover page, section [63], delete "Pat. No. 5,267,567", and insert therefor --Pat. No. 5,267,564--.

In col. 1, lines 2-4, delete the title "Multipolar In-Line Proximal Connector Assembly for an Implantable Stimulation Device", and insert therefor --An Implantable Stimulation Lead Having a Multipolar In-Line Proximal Assembly--.

In Claim 1, col. 13, lines 4-5, delete "at it proximal end", and insert therefor --at the proximal end--.

Signed and Sealed this

Fourth Day of July, 1995

*Attest:*

BRUCE LEHMAN

*Attesting Officer*  *Commissioner of Patents and Trademarks*